United States Patent [19]

Adams et al.

[11] Patent Number: 5,348,021
[45] Date of Patent: Sep. 20, 1994

[54] APPARATUS AND METHOD FOR RELIABLY DETECTING A DEPOLARIZATION ACTIVATION WAVE OF THE HEART AND ATRIAL DEFIBRILLATOR UTILIZING SAME

[75] Inventors: John M. Adams, Issaquah; Clifton A. Alferness; Kenneth R. Infinger, both of Redmond, all of Wash.

[73] Assignee: InControl, Inc., Redmond, Wash.

[21] Appl. No.: 861,184

[22] Filed: Mar. 31, 1992

[51] Int. Cl.⁵ .............................................. A61B 5/046
[52] U.S. Cl. ............................................................ 128/708
[58] Field of Search ............ 128/419 PG, 419 D, 708; 607/5, 9

[56] References Cited

U.S. PATENT DOCUMENTS

| | | | |
|---|---|---|---|
| 3,903,897 | 9/1975 | Woollons et al. | 128/419 PG |
| 4,091,818 | 5/1978 | Brownlee et al. | 128/419 PG |
| 4,250,889 | 2/1981 | Levin | 128/708 |
| 4,289,134 | 9/1981 | Bernstein | 128/419 PG |
| 4,365,639 | 12/1982 | Goldreyer | 128/419 PG |
| 4,416,282 | 11/1983 | Saulson et al. | 128/419 PG |
| 4,535,776 | 8/1985 | Strandberg | 128/419 PG |
| 4,543,963 | 10/1985 | Gessman | 128/419 PG |
| 4,577,634 | 3/1985 | Gessman | 128/419 PG |
| 4,759,366 | 7/1988 | Callaghan | 128/419 PG |
| 4,766,902 | 8/1988 | Schroeppel | 128/419 PG |
| 4,799,493 | 1/1989 | Dufault | 128/419 PG |
| 4,892,102 | 1/1990 | Astrinsky | 128/419 PG |
| 4,899,752 | 2/1990 | Cohen | 128/419 PG |
| 4,928,688 | 5/1990 | Moner | 128/419 PG |
| 5,014,696 | 5/1991 | Mehra | 128/419 D |
| 5,109,842 | 5/1992 | Adinolfi | 128/419 D |
| 5,184,614 | 2/1993 | Collins et al. | 128/419 D |

Primary Examiner—William E. Kamm
Attorney, Agent, or Firm—Foley & Lardner

[57] ABSTRACT

An atrial defibrillator reliably detects a depolarization activation wave of the heart and delivers cardioverting electrical energy to the atria of the heart in synchronism with a detected depolarization activation wave. The atrial defibrillator includes a first sensor for producing a first electrical output having a duration substantially equal to the duration of the depolarization activation wave sensed between a first pair of spaced apart locations of the heart. The atrial defibrillator further includes a second sensor for producing a second electrical output having a duration substantially equal to the duration of the depolarization activation wave sensed between a second pair of spaced apart locations of the heart. The spacing between the second pair of locations is greater than the spacing between the first pair of locations. A microprocessor is responsive to the first and second electrical outputs for providing an indication signal indicating the occurrence of the depolarization activation wave when the second electrical output is longer in duration than the first electrical output. A pulse generator coupled to the microprocessor applies electrical cardioverting energy to the atria of the heart in response to the indication signal.

58 Claims, 4 Drawing Sheets

APPARATUS AND METHOD FOR RELIABLY DETECTING A DEPOLARIZATION ACTIVATION WAVE OF THE HEART AND ATRIAL DEFIBRILLATOR UTILIZING SAME

BACKGROUND OF THE INVENTION

The present invention generally relates to an apparatus and method for detecting a depolarization activation wave (R wave) of the heart. The present invention is more particularly directed to an atrial defibrillator and method employing such an apparatus and method for reliably detecting a depolarization activation wave of the heart and delivering cardioverting electrical energy to the atria of the heart in synchronism with the detected depolarization activation wave.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying cardioverting or defibrillating electrical energy to the heart in synchronism with a detected depolarization activation wave (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, date, none of these atrial defibrillators have become a commercial realty to the detriment of such patients.

Implantable atrial defibrillators proposed in the past have exhibited a number of disadvantages which probably have been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Synchronizing the delivery of the defibrillating or cardioverting electrical energy with a depolarization activation wave (R wave) of the heart important to prevent ventricular fibrillation. Ventricular fibrillation is a fatal arrhythmia which can be caused by electrical energy being delivered to the heart at the wrong time in the cardiac cycle, such during the T wave of the cycle. As a result, it is most desirable to sense depolarization activation waves of the heart to generate synchronization pulses (or signals) a manner which avoids detecting noise as a depolarization activation wave. Unfortunately, until recently, implantable atrial defibrillators which have been proposed have not provided either such noise immunity any other means for assuring reliable synchronization.

One recently proposed atrial defibrillator which does provide reliable and noise immune detection of depolarization activation waves of the heart and delivery of electrical cardioverting or defibrillating electrical energy to the atria of the heart in synchronism with a detected depolarization activation wave is fully described in copending U.S. application Ser. No. 07/685,130 filed Apr. 12, 1991, in the names John M. Adams and Clifton A. Alferness and entitled ATRIAL DEFIBRILLATOR AND METHOD, which application assigned to the assignee of the present invention and incorporated herein by reference. The atrial defibrillator there disclosed includes first means sensing depolarization activation waves at a first of the heart and second means for sensing the depolarization activation waves at a second area of the heart. The atrial defibrillator further includes detector for detecting non-coincident sensing cf depolarization activation wave at the first area of the heart by the first sensing means and at the second area of the heart by the second sensing means. The atrial defibrillator further includes storage means for storing electrical energy and delivery means coupled to the storage means and being responsive to the non-coincident sensing of a depolarization activation wave at the first and second areas of the heart for applying predetermined amount of stored electrical energy to the atria for cardioverting or defibrillating the heart. Reliable and noise immune detection of the depolarization activation waves is provided by the non-coincident sensing of the depolarization activation waves which would be mistaken for a depolarization activation wave by prior atrial defibrillators is not mistaken a depolarization activation wave because such noise would be sensed coincidently by the first and second sensing means at the first and second areas of the heart. Hence, by the non-coincident sensing of the depolarization activation waves and the non-coincident detection thereof by the detector, the above atrial defibrillator capable of reliably detecting depolarization activation waves in a manner which is immune to noise. The apparatus and method of the present invention represents an alternative approach to reliable detection of depolarization activation waves of the heart and the delivery of electrical cardioverting energy to the atria of the heart in synchronism with a detected depolarization activation wave.

SUMMARY OF THE INVENTION

The present invention therefore provides an apparatus for reliably detecting a depolarization activation wave of the heart. The apparatus includes first sensing means in electrical contact with the heart for producing a first electrocardiogram of the heart and first output means coupled to the first sensing means and responsive to the first electrocardiogram for isolating a predetermined feature of the first electrocardiogram and producing a first output characteristic of the feature of the first electrocardiogram. The apparatus further includes second sensing means in electrical contact with the heart for producing a second electrocardiogram of the heart, and second output means coupled to the second sensing means and responsive to the second electrocardiogram for isolating the predetermined feature of the second electrocardiogram and producing a second output characteristic of the feature of the second electrocardiogram. The apparatus further includes discriminating means coupled to the first and second output means and responsive to said first and second electrical outputs for discriminating between the predetermined features of the first and second electrocardiograms and for indicating the occurrence of the depolarization activation wave when the predetermined features of said first and second electrocardiograms are different.

The present invention further provides a method of reliably detecting a depolarization activation wave of the heart. The method includes the steps of sensing electrical activity of the heart at a first location of the heart and producing a first electrocardiogram and isolating a predetermined feature of the first electrocardiogram and producing a first output characteristic of the feature of the first electrocardiogram. The method further includes the steps of sensing the electrical activity of the heart at a second location of the heart and producing a second electrocardiogram, isolating the predetermined feature of the second electrocardiogram and producing a second output characteristic of the feature of the second electrocardiogram, and discriminating between the predetermined features of the first and second electrocardiograms and indicating the occurrence of the depolarization activation wave when the predetermined features of said first and second electrocardiograms are different.

The present invention also provides an apparatus for reliably detecting a depolarization activation wave of the heart. The apparatus includes first sensing means in electrical contact with the heart between a first pair of spaced apart locations for sensing the depolarization activation wave and first output means coupled to the first sensing means for producing a first electrical output having a first predetermined characteristic corresponding to the depolarization activation wave sensed by the first sensing means. The apparatus further includes second sensing means in electrical contact with the heart between a second pair of spaced apart locations for sensing the depolarization activation wave, second output means coupled to the second sensing means for producing a second electrical output having a second predetermined characteristic corresponding to the depolarization activation wave sensed by the second sensing means, and discriminating means coupled to the first and second output means and being responsive to the first and second electrical outputs for discriminating between the first and second predetermined characteristics and for indicating the occurrence of the depolarization activation wave when the first and second predetermined characteristics are different.

The present invention further provides an atrial defibrillator for reliably detecting a depolarization activation wave of the heart and delivering cardioverting electrical energy to the atria of the heart in synchronism with the detected depolarization activation wave. The atrial defibrillator includes first sensing means in electrical contact with the heart between a first pair of spaced apart locations for sensing the depolarization activation wave and first output means coupled to the first sensing means for producing a first electrical output having a first predetermined characteristic corresponding to the depolarization activation wave sensed by the first sensing means. The atrial defibrillator further includes second sensing means in electrical contact with the heart between a second pair of spaced apart locations for sensing the depolarization activation wave and second output means coupled to the second sensing means for producing a second electrical output having a second predetermined characteristic corresponding to the depolarization activation wave sensed by the second sensing means. The atrial defibrillator further includes discriminating means coupled to the first and second output means and being responsive to the first and second electrical outputs for discriminating between the first and second predetermined characteristics and for providing an indication signal indicating the occurrence of the depolarization activation wave when the first and second predetermined characteristics are different and delivery means coupled to the discriminating means and responsive to the indication signal for applying electrical cardioverting energy to the atria of the heart.

The present invention further provides a method of reliably detecting a depolarization activation wave of the heart. The method includes the steps of sensing the depolarization activation wave of the heart between a first pair of spaced apart locations, producing a first electrical output having a first predetermined characteristic corresponding to the depolarization activation wave sensed between said first pair of locations, sensing the depolarization activation wave of the heart between a second pair of spaced apart locations, producing a second electrical output having a second predetermined characteristic corresponding to the depolarization activation wave sensed between the second pair of locations, and indicating the occurrence of the depolarization activation wave when the first and second predetermined characteristics are different.

The present invention further provides a method of reliably detecting a depolarization activation wave of the heart and delivering cardioverting electrical energy to the atria of the heart in synchronism with the detected depolarization activation wave. The method includes the steps of sensing the depolarization activation wave of the heart between a first pair cf spaced apart locations, producing a first electrical output having a first predetermined characteristic corresponding to the depolarization activation wave sensed between the first pair of locations, sensing the depolarization activation wave of the heart between a second pair of spaced apart locations, and producing a second electrical output having a second predetermined characteristic corresponding to the depolarization activation wave sensed between the second pair of locations. The method further includes the steps of providing an indication signal indicating the occurrence of the depolarization activation wave when the first and second predetermined characteristics are different, and applying electrical cardioverting energy to the atria of the heart responsive to the indication signal.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENTS

Figure 1:
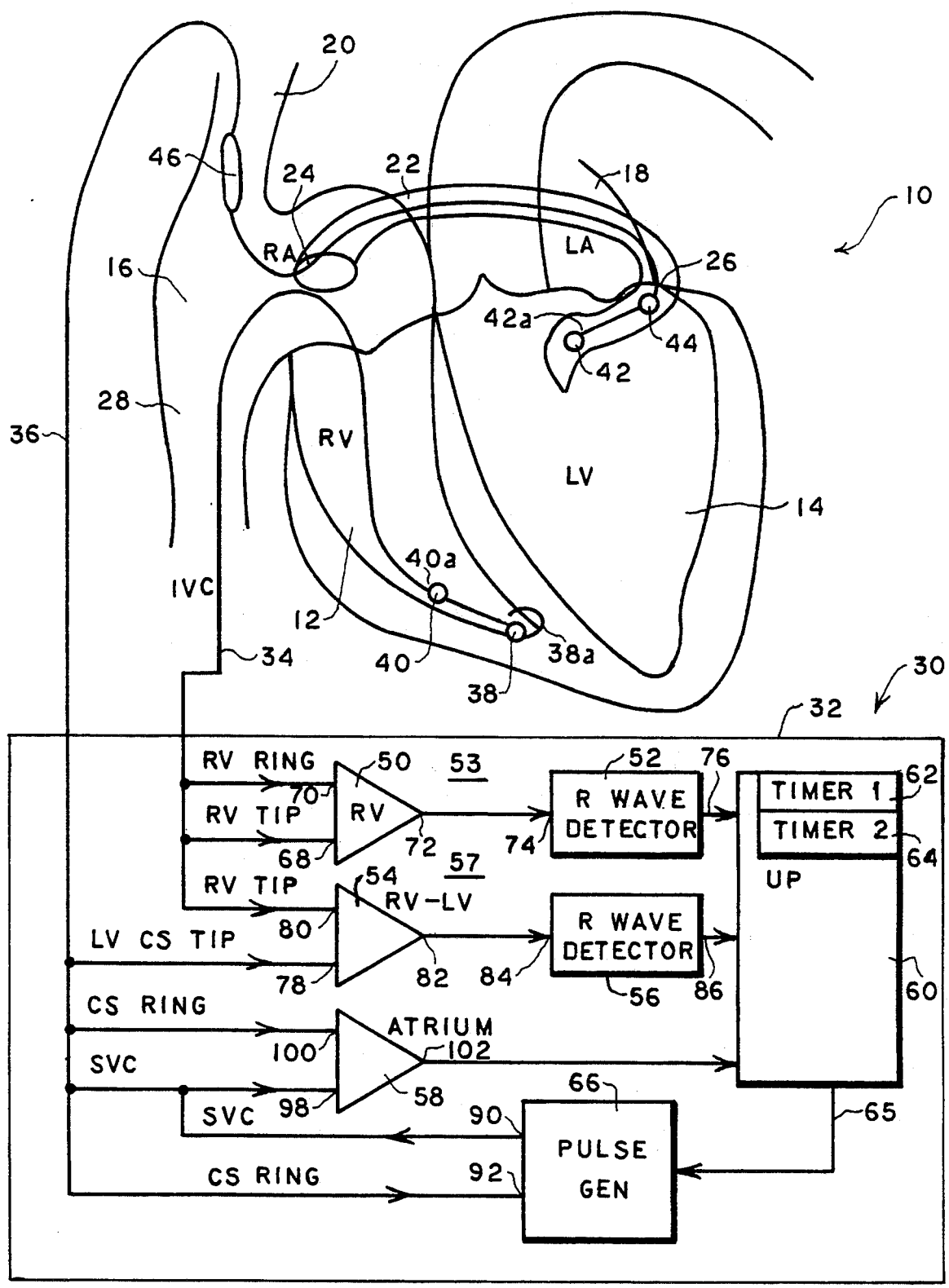
FIG. 1 is a schematic block diagram of a fully implantable atrial defibrillator embodying the present invention in accordance with a first preferred embodiment thereof and shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus 22, the coronary sinus ostium or opening 24, the left ventricular free wall 26, and the inferior vena cava 28. In addition, as used herein, the term "depolarization activation waves" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator, an endocardial first lead 34, and an intravascular second lead 36. The enclosure 32 and first and second leads and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of depolarization activation waves in the right ventricle between a first pair of locations 38a and 40a within the right ventricle 12. As illustrated, the lead 34 is fed through the inferior vena cava 28, into the right atrium 16, and then into the right ventricle 12. As will be appreciated by those skilled in the art, a second path for lead 34 could alternatively be through the superior vena cava 20, into the right atrium 16, and then into the right ventricle 12.

The second lead 36 generally includes a first or distal electrode 42, a second or ring electrode 44, and a third electrode 46. As illustrated, the second lead 36 is flexible and arranged to be passed down the superior vena cava 20, into the right atrium 16, into the coronary sinus ostium 24, and advanced into the coronary sinus 22 of the heart near the left side thereof so that the first or distal electrode 42 is within the coronary sinus or within a coronary vein, such as the great vein of the heart (not shown) adjacent the left ventricle 14. The electrodes 42, 44, and 46 are spaced apart such that when the first electrode 42 is within the coronary 22 or a coronary vein adjacent the left ventricle 14, the second electrode 44 is beneath the left atrium 18 near the left ventricle 14 and the third electrode 46 within either the right atrium 16 or the superior vena cava 20 and preferably within the right atrium 16.

The first electrode 42 of the second lead and the electrode 38 of the first lead 34 permit bi-polar sensing of depolarization activation waves between second pair of locations 38a and 42a of the heart. Alternatively, the second pair of electrodes may include electrodes 42 and 40 and, as a result, the second pair of locations may be locations 42a and 40a. As will be noted in FIG. 1, the spacing between the second pair of locations 38a and 42a is greater than the spacing between the first pair of locations 38a and 40a. As will be seen hereinafter, these relative spacings between the first and second pairs of locations between which depolarization activation waves are sensed enable reliable detection of depolarization activation waves in accordance with the present invention.

The second electrode 44 together with the third electrode 46 of the second lead 36 provide for the delivery of defibrillating or cardioverting electrical energy to the atria. Because the second electrode 44 located beneath the left atrium 18 near the left ventricle 14 and the third electrode 46 is within either the right atrium 16 or the superior vena cava 20 and above the coronary sinus ostium 24, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized.

Within the enclosure 32, the atrial defibrillator 30 includes a first sense amplifier 50, a first R wave detector 52, a second sense amplifier 54, a second R wave detector 56 and a third sense amplifier 58. Within the enclosure 32, the atrial defibrillator 30 also includes a microprocessor 60 and a pulse generator 66. As also can be seen in FIG. 1, the microprocessor includes a first timer 62 and a second timer 64.

The first sense amplifier 50 includes a first input 68 which is coupled to electrode 38 of the first lead 34 and a second input 70 which is coupled to electrode 40 of the first lead 34. The first sense amplifier 50 thus senses the electrical activity of the heart 10 between the first pair of locations of the heart 38a and 40a. It amplifies the sensed electrical activity of the heart and provides at an output 72 an amplified signal or first electrocardiogram representative of the electrical activity of the heart sensed by the bi-polar electrodes 38 and 40.

The first R wave detector 52 includes an input 74 which is coupled to the output 72 of the first amplifier 50. The R wave detector 52 includes a threshold detecting means or circuit which provides a substantially constant first electrical output having a duration substantially equal to the duration of the depolarization activation waves (R waves) sensed between electrodes 38 and 40. As a result, the electrodes 38 and 40 and the first sense amplifier 50 form a first sensing means 53 for sensing electrical activity of the heart including depolarization activation waves between the first pair of spaced apart locations of the heart 38a and 40a. The first R wave detector 52 forms a first output means for isolating the R wave feature of the first electrocardiogram and for producing a first electrical output, at output 76, having a first predetermined characteristic or duration corresponding and substantially equal to the duration of the depolarization activation waves (R waves) sensed between the first pair or locations of the heart 38a and 40a.

The second sense amplifier 54 includes a first input 78 which is coupled to the electrode 42 of the second lead 36 and a second input 80 which is coupled to electrode 38 of the first lead 34. As a result, the second sense amplifier 54 senses the electrical activity of the heart between the second pair of locations of the heart 38a and 42a. It provides at an output 82 an amplified signal or second electrocardiogram representative of the electrical activity of the heart sensed between the second pair of locations of the heart 38a and 42a.

The second R wave detector 56 includes an input 84 for receiving the amplified signal provided from the output 82 of the second sense amplifier 54. The second R wave detector 56 also includes a second threshold detecting means or circuit for providing a substantially constant second electrical output at output 86 having a duration substantially equal to the duration of the depolarization activation waves sensed by the second sense amplifier 54. As a result, electrode 42, electrode 38, and sense amplifier 54 form a second sensing means 57 for sensing electrical activity of the heart including depolarization activation waves between the second pair of locations of the heart 38a and 42a. The second R wave detector 56 forms a second output means for isolating the R wave feature of the second electrocardiogram for producing a second electrical output having a second predetermined characteristic or duration corresponding and substantially equal to the duration of the depolarization activation waves (R waves) sensed between the second pair of locations of the heart 38a and 42a.

When the heart 10 is in need of cardioversion or defibrillation, the first timer 62 times the duration of the first electrical output of the first electrical output provided by the first R wave detector 52 for timing the duration of a depolarization activation wave (R wave) sensed between the first pair of locations 38a and 40a. The second timer 64 also times the duration of the second electrical output provided by the second R wave detector 56 for timing the duration of the same depolarization activation wave (R wave) sensed between the second pair of locations 42a and 38a. Since the spacing between the second pair of locations 42a and 38a is greater than the spacing between the first pair of locations 40a and 38a, if the electrical activity of the heart sensed by the first sensing means 53 and second sensing means 57 is a true depolarization activation wave (R wave), the duration of the second electrical output provided by R wave detector 56 will be longer than the duration of the first electrical output provided by the first R wave detector 52. Hence, the predetermined features (R waves) of the first and second electrocardiograms and more specifically, the first and second predetermined characteristics (durations) of those features will be different.

If the second electrical output is longer in duration than the first electrical output, the microprocessor 60 immediately provides an indication signal on line 65 indicating that a depolarization activation wave (R wave) has been detected. Thus, the microprocessor 60 forms a discriminating means which responsive to the first and second electrical outputs for providing an indication signal indicating the occurrence of the depolarization activation wave. The microprocessor 60 discriminates between a depolarization activation wave and noise responsive to the second electrical output having a duration which is longer than the duration of the first electrical output. If the electrical activity of the heart sensed by the first and second sensing means 53 and 57 respectively is noise, a characteristic of the first and second electrical outputs, such as duration, will be substantially the same. As a result, when noise is detected, the microprocessor 60 will not provide the indication signal over line 65.

The pulse generator 66 is of the type well known in the art which includes a storage capacitor for storing an electrical charge. Upon receiving the indication signal from the microprocessor 60 over line 65, the pulse generator 66 delivers electrical cardioverting energy to the atria of the heart. To that end, the pulse generator 66 includes a first output 90 which is coupled to electrode 46 of the second lead and a second output 92 which is coupled to electrode 44 of the second lead 36. As a result, the electrodes 44 and 46 of the second lead 36 apply the electrical cardioverting energy provided by the pulse generator to the atria 16 and 18 of the heart 10.

To determine when cardioversion defibrillation of the atria of the heart 10 is required, the third sense amplifier 58 senses electrical activity in the atria 16 and 18 of the heart 10. To that end, the third sense amplifier 58 includes a first input 98 which is coupled to electrode 46 and a second input 100 which is coupled to electrode 44. The third sense amplifier 58 includes an output 102 which is coupled to the microprocessor 60 for providing the microprocessor 60 with an amplified signal representing the electrical activity of the atria 16 and 18 of the heart.

The microprocessor 60, as described in the aforementioned copending U.S. application Ser. No. 07/685,131, digitizes the amplified electrical signal provided by the third sense amplifier 58 and processes the digitized values of the atrial activity for detecting atrial fibrillation. Such atrial fibrillation detection may be implemented by the microprocessor 60 as described in the aforementioned copending application. Alternatively, the microprocessor 60 may be implemented in accordance with the atrial fibrillation detection algorithms disclosed in a paper: Janice Jenkins, Ki Hong Noh, Alain Guezennec, Thomas Bump, and Robert Arzbaecher, "Diagnosis of Atrial Fibrillation Using Electrograms from Chronic Leads: Evaluation of Computer Algorithms," *PACE*, Vol. 11, pp. 622-631, May, 1988. Implementing such algorithms by a microprocessor such as microprocessor 60 is well within the purview of one skilled in the art.

Figure 2:
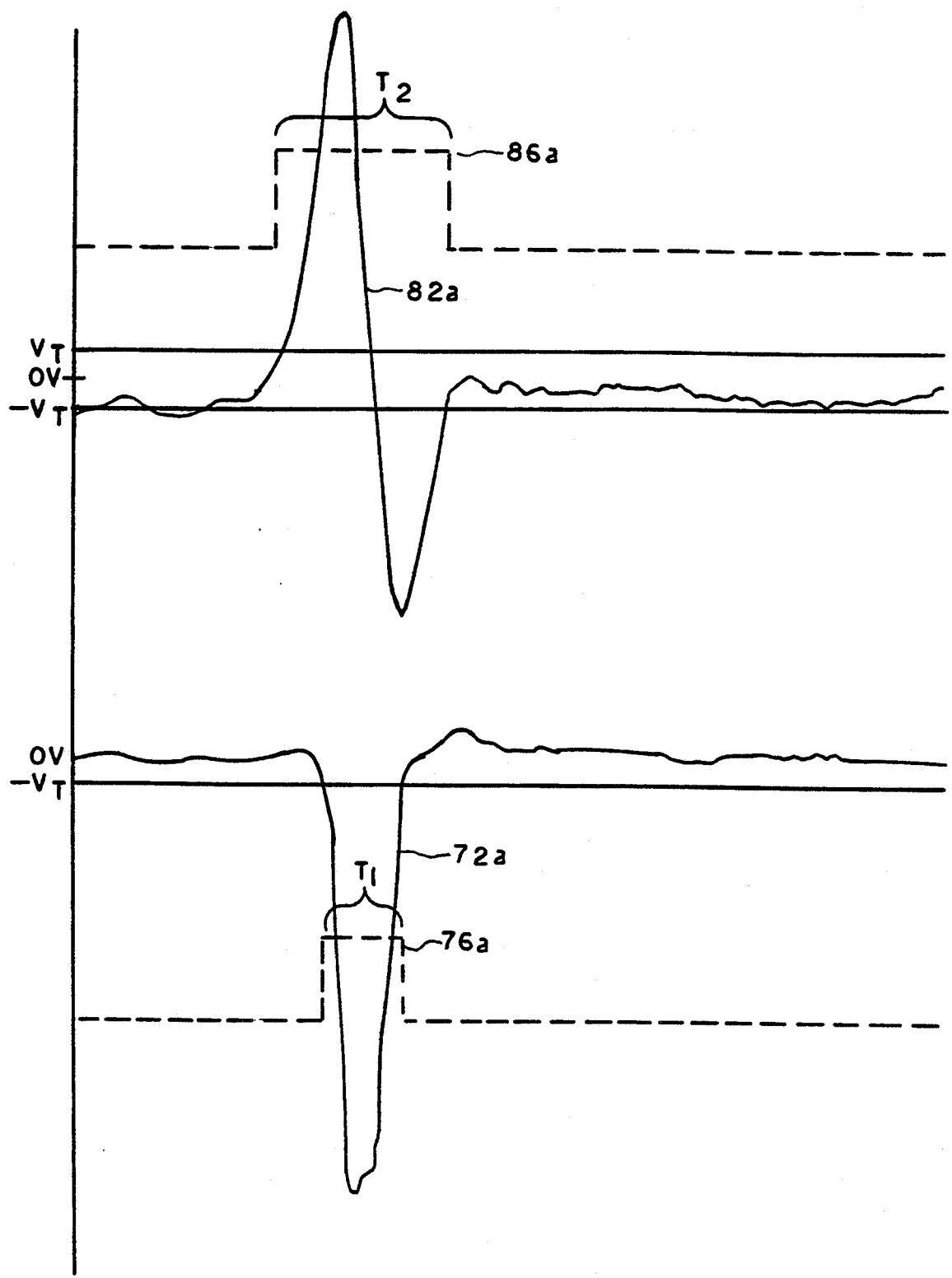
FIG. 2 is a series of waveforms illustrating representative electrocardiograms of a cardiac cycle of the heart including a depolarization activation wave sensed between first and second pairs of locations of the heart illustrated in FIG. 1 and first and second generated electrical outputs having durations substantially equal to the durations of the depolarization activation wave of the electrocardiogram as sensed between the first and second pairs of locations of the heart.

Referring now to FIG. 2, it illustrates a first amplified electrocardiogram signal 72a provided the first sense amplifier 50, a first electrical output 76a provided by the first R wave detector 52, a second amplified electrocardiogram signal 82a provided by the second sense amplifier 54, and a second electrical output 86a provided by the second R wave detector 56. All the foregoing waveforms are generated responsive to the detection of the same electrical activity of the heart including a depolarization activation wave (R wave). As will be noted from FIG. 2, when the first amplified signal 72a exceeds a voltage threshold ($V_t$) established by R wave detector 52, the R wave feature of the first electrocardiogram is isolated and the R wave detector 52 provides the first electrical output 76a having a duration of $T_1$. Similarly, when the second amplified signal 82a provided by sense amplifier 54 exceeds a threshold voltage ($V_t$) established by R wave detector the R wave feature of the second electrocardiogram isolated and the R wave detector 56 provides the second electrical output 86a having a duration of $T_2$. As can be appreciated by those skilled in the art, the R wave detectors 52 and 56 should have a relatively slow response to changes in input voltage amplitude to render the electrical outputs substantially constant amplitude notwithstanding zero crossings of the amplified electrical signals as is evident by amplified electrical signal 82a. As will be noted in FIG. 2, the duratic, n ($T_2$) of the second electrical output 86a is longer than the duration ($T_1$) of the first electrical output 76a. Given such inputs to the microprocessor 60, the microprocessor determines that the R wave features of the first and second electrocardiograms are different because $T_2$ is greater than $T_1$ and hence determines that legitimate depolarization activation wave (R wave) has been detected. Immediately following such a determination, the microprocessor 60 provides the indication signal on line 65 indicating that a legitimate depolarization activation wave has been detected.

Figure 3:
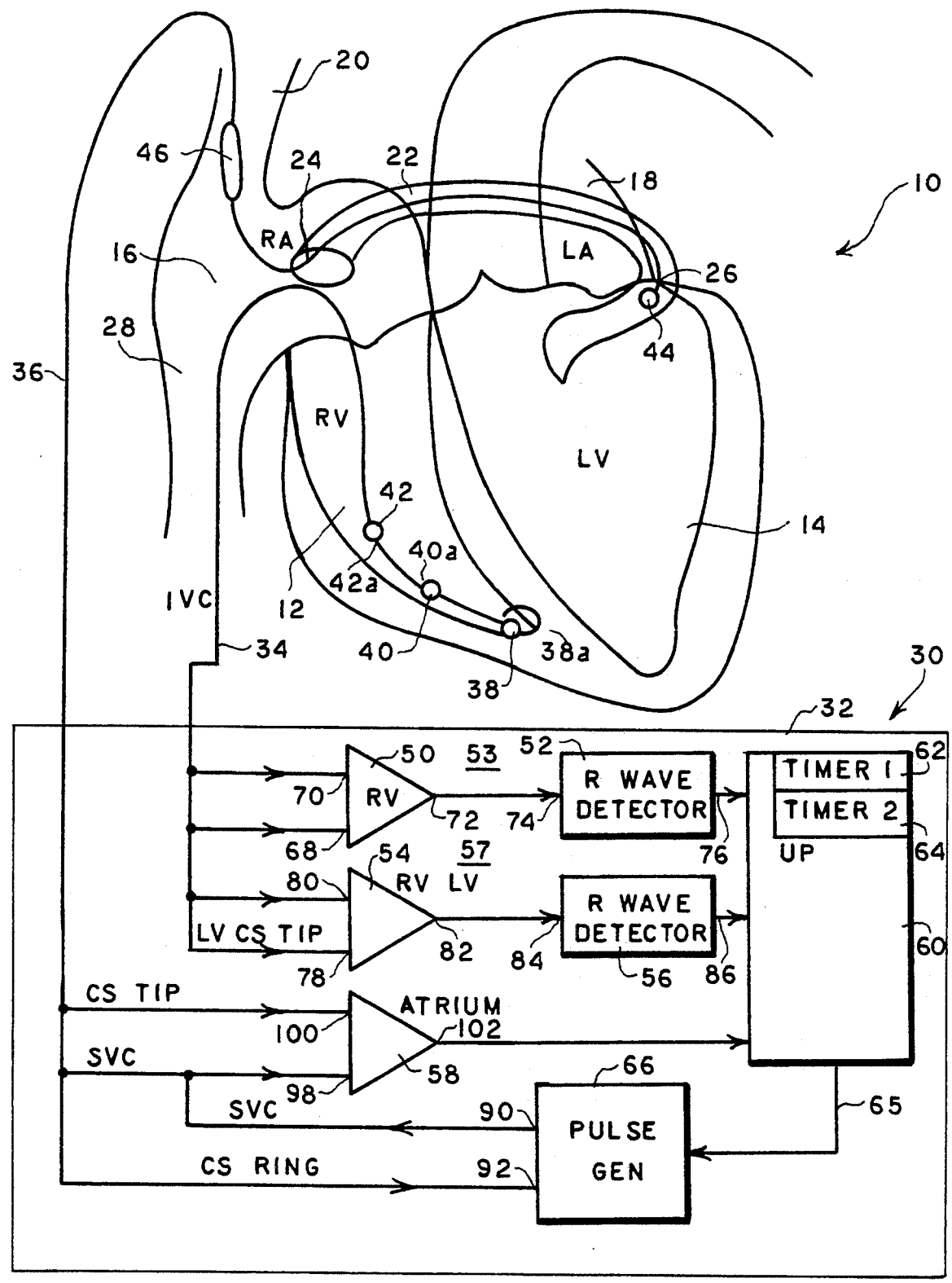
FIG. 3 is a schematic block diagram similar to FIG. 1 illustrating a second preferred embodiment of the present invention.

Referring now to FIG. 3, it illustrates a second preferred embodiment of the present invention. As will be noted in FIG. 3, the configuration of the atrial defibrillator 30 within enclosure 32 is the same as that illustrated in FIG. 1. As a result, like reference numerals to indicate identical elements are carried throughout FIG. 3.

It will be noted from FIG. 3, however, that sensing electrode 42, instead of being incorporated within the second lead 36, is now incorporated within the first lead 34. As a result, all three electrodes 38 40, and 42 for sensing electrical activity including depolarization activation waves of the heart 10 are carried on a single lead, lead 34, and are all disposed for electrical contact with the heart within the right ventricle 12.

Inputs 68 and 70 of sense amplifier 50 are still coupled to electrodes 38 and 40 respectively of the first lead 34. As a result, the first sense amplifier 50 senses electrical activity of the heart 10 between electrodes 38 and 40 and hence between the first pair of locations of the heart 38a and 40a. Input 80 of second sense amplifier 54 is still coupled to electrode 38 of lead 34, but now, input 78 of second sense amplifier 54 is coupled to electrode 42 which is now carried by the first lead 34. As a result, the second sense amplifier 54 senses electrical activity of the heart between electrodes 38 and 42 and hence between the second locations of the heart 38a and 42a. As will be noted from the Figure, since electrode 42 is of greater distance from electrode 38 than is electrode 40, the spacing between the second pair of locations 38a and 42a is greater than the spacing between the first pair of locations 38a and 40a. As a result, when a depolarization activation wave (R wave) is sensed by sense amplifiers 50 and 54, waveforms similar to that shown in FIG. 2 will result. Hence, the overall operation of the atrial defibrillator 30 as shown in FIG. 3 is the same as the overall operation of the atrial defibrillator as illustrated in FIG. 1. The electrical cardioverting energy is still applied to the atria 16 and 18 between electrodes 44 and 46 and atrial activity of the heart is also sensed between electrodes 44 and 46.

Figure 4:
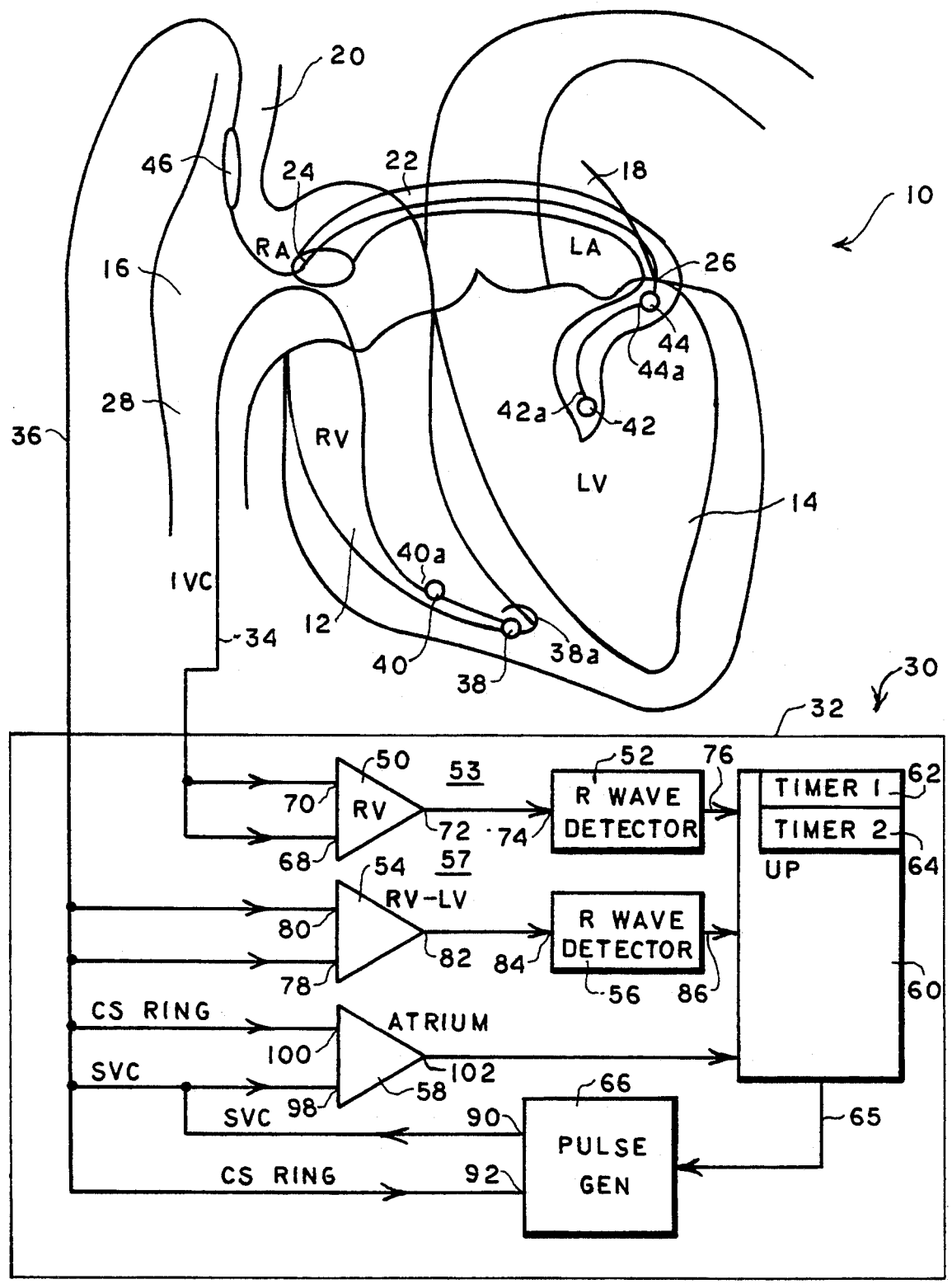
FIG. 4 is a schematic block diagram similar FIG. 1 illustrating a third preferred embodiment of the present invention.

Referring now to FIG. 4, it illustrates a third preferred embodiment of the present invention. Again, the configuration of the atrial defibrillator 30 within enclosure 32 is essentially identical to the configuration of the atrial defibrillator as illustrated in FIG. 1 and therefore, again, like reference numerals indicating like elements are carried throughout FIG. 4. While in the first and second embodiments of FIGS. 1 and 3 respectively the first and second pairs of locations between which electrical activity of the heart is sensed are defined by the locations of three electrodes, with the location of one electrode being in common to both pairs of locations, the first and second pairs of locations between which electrical activity of the heart is sensed in FIG. 4 are defined by the locations of four electrodes. To that end, it will be noted that inputs 68 and 70 of the first sense amplifier 50 are still coupled to electrodes 38 and 40 for sensing electrical activity of the heart between locations 38a and 40a. However, input 78 of second sense amplifier 54 is coupled to electrode 42 of the second lead 36 and input 80 of second sense amplifier 54 is now coupled to electrode 44 of the second lead 36. As a result, the second sense amplifier 54 senses heart activity between a second pair of locations of the heart 42a and 44a. In addition, the second lead 36 is fed further down the coronary sinus 22 such that the spacing between electrodes 42 and 44 is greater than the spacing between electrodes 38 and 40. As a result, the spacing between the second pair of locations 42a and 44a is greater than the spacing between the first pair of locations 38a and 40a. Also, and as a result, the first pair of locations 38a and 40a are still in the right ventricle while the second pair of locations 42a and 44a are in the left ventricle.

In all other respects, the operation of the atrial defibrillator 30 may remain the same as previously described. Electrodes 46 and 44 may still be utilized for applying cardioverting or defibrillating electrical energy to the atria 16 and 18 of the heart 10 and electrodes 44 and 46 may still be utilized for detecting atrial activity of the heart for detecting atrial fibrillation.

While particular embodiments of the present invention have been shown and described, modifications may be made. For example, unipolar sensing may be employed for establishing the first or second pair of sensing location. More specifically, in the embodiment of FIG. 1, the second pair of sensing locations may be established between electrode 38 and the enclosure of the atrial defibrillator 30. Furthermore, any electrocardiogram feature may be isolated for discrimination purposes. For example, the Q wave feature of the electrocardiogram or the Q wave to R wave relation may be isolated and utilized for discrimination. Such discrimination may be based upon most any difference in such features such as, amplitude, duration, or polarity, for example. Therefore it is intended in the appended claims to cover all such changes and modifications which fall within the true spirit and scope of the invention.

What is claimed is:

1. An apparatus for reliably detecting a depolarization activation wave of the heart, said apparatus comprising:

first sensing means for electrical contact with the heart for between a first pair of spaced apart locations for sensing said depolarization activation wave;

first output means coupled to said first sensing means for producing a first electrical output having a first predetermined characteristic corresponding to said depolarization activation wave sensed by said first sensing means;

second sensing means for electrical contact with the heart between a second pair of spaced apart locations for sensing said depolarization activation wave;

second output means coupled to said second sensing means for producing a second electrical output having a second predetermined characteristic corresponding to said depolarization activation wave sensed by said second sensing means; and discriminating means coupled to said first and second output means and being responsive to said first and second electrical outputs for discriminating between said first and second predetermined characteristics and including indicating means for indicating the occurrence of said depolarization activation wave when said first and second predetermined characteristics are different.

2. An apparatus as defined in claim 1 wherein the spacing between said first pair of locations is different than the spacing between said second pair of locations, wherein said first output means includes first threshold means for providing said first electrical output with a duration substantially equal to the time in which said depolarization activation wave sensed by said first sensing means is above a given threshold, wherein said second output means includes second threshold means for providing said second electrical output with a duration substantially equal to the time in which said depolarization activation wave sensed by said second sensing means is above said given threshold, and wherein said first and second predetermined characteristics are the durations of said first and second electrical outputs respectively.

3. An apparatus as defined in claim 2 wherein said spacing between said second pair of locations is greater than the spacing between said first pair of locations and wherein said indicating means indicates the occurrence of said depolarization activation wave when the duration of said second electrical output is longer than the duration of said first electrical output.

4. An apparatus as defined in claim 1 further including first, second, and third electrodes for electrical contact with the heart, wherein said first sensing means including said first and second electrodes for sensing said depolarization activation wave between said first pair of locations and said second sensing means includes one of said first and second electrodes and said third electrode for sensing said depolarization activation wave between said second pair of locations.

5. An apparatus as defined in claim 4 further including a first lead including said first and second electrodes and a second lead including said third electrodes.

6. An apparatus as defined in claim 5 wherein said first lead is configured for disposing said first and second electrodes for electrical contact with the right ventricle of the heart and wherein said second lead is configured for disposing said third electrode for electrical contact with the left ventricle of the heart.

7. An apparatus as defined in claim 4 further including a single lead means including said first, second, and third electrodes.

8. An apparatus as defined in claim 7 wherein said first, second, and third electrodes are in electrical contact with the right ventricle of the heart.

9. An apparatus as defined in claim 4 wherein said first output means includes a first threshold detector for providing said first electrical output and wherein said second output means includes a second threshold detector for providing said second electrical output.

10. An apparatus as defined in claim 9 wherein said first sensing means further includes a first sense amplifier coupled between said first and second electrodes and said first threshold detector and wherein said second sensing means includes a second sense amplifier coupled between said one of said first and second electrodes and said third electrode and said second threshold detector.

11. An apparatus as defined in claim 1 wherein said first sensing means includes first and second electrodes in electrical contact with the heart for sensing said depolarization activation wave between said first pair of locations and said second sensing means includes third and fourth electrodes in electrical contact with the heart for sensing said depolarization activation wave between said second pair of locations.

12. An apparatus as defined in claim 11 further including first lead means including said first and second electrodes and second lead means including said third and fourth electrodes.

13. An apparatus as defined in claim 12 wherein said first and second electrodes are electrical contact with the right ventricle of the heart and wherein said third and fourth electrodes are electrical contact with the left ventricle of the heart.

14. An apparatus as defined in claim 11 wherein said first output means includes first threshold detecting means for providing said first electrical output and wherein said second output means includes a second threshold detecting means for providing said second electrical output.

15. An apparatus as defined in claim 14 wherein said first sensing means further includes a first sense amplifier coupled between said first and second electrodes and said first threshold detecting means and wherein said second sensing means includes a second sense amplifier coupled between said third and fourth electrodes and said second threshold detecting means.

16. An atrial defibrillator for reliably detecting a depolarization activation wave of the heart and delivering cardioverting electrical energy to the atria of the heart in synchronism with said detected depolarization activation wave, said atrial defibrillator comprising:

first sensing means for electrical contact with the heart between a first pair of spaced apart locations for sensing said depolarization activation wave;

first output means coupled to said first sensing means for producing a first electrical output having a first predetermined characteristic corresponding to said depolarization activation wave sensed by said first sensing means;

second sensing means for electrical contact with the heart between a second pair of spaced apart locations for sensing said depolarization activation wave;

second output means coupled to said second sensing means for producing a second electrical output having a second predetermined characteristic corresponding to said depolarization activation wave sensed by said second sensing means;

discriminating means coupled to said first and second output means and being responsive to said first and second electrical outputs for discriminating between said first and second predetermined characteristics and including indicating means for providing an indication signal indicating the occurrence of said depolarization activation wave when said first and second predetermined characteristics are different; and delivery means coupled to said discriminating means and responsive to said indication signal for applying electrical cardioverting energy to the atria of the heart.

17. An atrial defibrillator as defined in claim 16 wherein the spacing between said first pair of locations is different than the spacing between said second pair of locations, wherein said first output means includes first threshold means for providing said first electrical output with a duration substantially equal to the time in which said depolarization activation wave sensed by said first sensing means is above a given threshold, wherein said second output means includes second threshold means for providing said second electrical output with a duration substantially equal to the time in which said depolarization activation wave sensed by said second sensing means is above said given threshold, and wherein said first and second predetermined characteristics are the durations of said first and second electrical outputs respectively.

18. An atria; defibrillator as defined in claim 17 wherein said spacing between said second pair of locations is greater than the spacing between said first pair of locations and wherein said indicating means indicates the occurrence of said depolarization activation wave when the duration of said second electrical output is longer than the duration of said first electrical output.

19. An atrial defibrillator as defined in claim 16 further including first, second, and third electrodes for electrical contact with the heart, wherein said first sensing means includes said first and second electrodes for sensing said depolarization activation wave between said first pair of locations and said second sensing means includes one of said first and second electrodes and said third electrode for sensing said depolarization activation wave between said second pair of locations.

20. An atrial defibrillator as defined in claim 19 further including a first lead including said first and second electrodes and a second lead including said third electrodes.

21. An atrial defibrillator as defined in claim 20 wherein said first lead is configured for disposing said first and second electrodes for electrical contact with the right ventricle of the heart and wherein said second lead is configured for disposing said third electrode for electrical contact with the left ventricle of the heart.

22. An atrial defibrillator as defined in claim 19 further including a single lead means including said first, second, and third electrodes.

23. An atrial defibrillator as defined in claim 22 wherein said first, second, and third electrodes are in electrical contact with the right ventricle of the heart.

24. An atrial defibrillator as defined in claim 196 wherein said first output means includes a first threshold detector for providing said first electrical output and wherein said second output means includes a second threshold detector for providing said second electrical output.

25. An atrial defibrillator as defined in claim 24 wherein said first sensing means further includes a first sense amplifier coupled between said first and second electrodes and said first threshold detector and wherein said second sensing means includes a second sense amplifier coupled between said one of said first and second electrodes and said third electrodes and said second threshold detector.

26. An atrial defibrillator as defined in claim 16 wherein said first sensing means includes first and second electrodes in electrical contact with the heart for sensing said depolarization activation wave between said first pair of locations and said second sensing means includes third and fourth electrodes in electrical contact with the heart for sensing said depolarization activation wave between said second pair of location.

27. An atrial defibrillator as defined in claim 26 further including first lead means including said first and second electrodes and second lead means including said third and fourth electrodes.

28. An atrial defibrillator as defined claim 27 wherein said first and second electrodes are electrical contact with the right ventricle of the heart and wherein said third and fourth electrodes are in electrical contact with the left ventricle of the heart.

29. An atrial defibrillator as defined in claim 26 wherein said first output means includes first threshold detecting means for providing said first electrical output and wherein said second output means includes a second threshold detecting means for providing said second electrical output.

30. An atrial defibrillator as defined in claim 29 wherein said first sensing means further includes a first sense amplifier coupled between said first and second electrodes and said first threshold detecting means and wherein said second sensing means includes a second sense amplifier coupled between said third and fourth electrodes and said second threshold detecting means.

31. A method of reliably detecting a depolarization activation wave of the heart, said method including the steps of:
sensing said depolarization activation wave of the heart between a first pair of spaced apart locations;
producing a first electrical output having a first predetermined characteristic corresponding to said depolarization activation wave sensed between said first pair of locations;
sensing said depolarization activation wave of the heart between a second pair of spaced apart locations;
producing a second electrical output having a second predetermined characteristic corresponding to the said depolarization activation wave sensed between said second pair of locations;
comparing said first and second predetermined characteristics; and
indicating the occurrence of said depolarization activation wave when said first and second predetermined characteristics are different.

32. A method as defined in claim 31 wherein the spacing between said first pair of locations is different than the spacing between said second pair of locations, wherein said steps of providing said first and second electrical outputs include the step of providing said first and second electrical outputs with durations substantially equal to the time in which said depolarization activation wave sensed between said first and second pairs of locations respectively is above a given level, and wherein said first and second predetermined characteristics are the durations of said first and second electrical outputs respectively.

33. A method as defined in claim 32 wherein said spacing between said second pair of locations is greater than the spacing between said first pair of locations and wherein said indicating step includes indicating the occurrence of said depolarization activation wave when said second electrical output is longer in duration than said first electrical output.

34. A method as defined in claim 31 wherein said first pair of locations are between first and second locations and wherein said second pair of locations are between one of said first and second locations and a third location.

35. A method as defined in claim 34 further including the steps of providing first lead means including first and second electrodes, providing second lead means including a third electrode, and establishing electrical contact of said first, second, and third electrodes with the heart of said first, second, and third locations respectively.

36. A method as defined in claim 35 wherein said first and second electrodes are in electrical contact with the right ventricle of the heart and wherein said third electrode is in electrical contact with the left ventricle of the heart.

37. A method as defined in claim 34 further including the steps of providing a single lead means including first, second, and third electrodes and establishing electrical contact of said first, second, and third sensing electrodes with the heart at said first, second, and third locations respectively.

38. A method as defined in claim 37 wherein said first, second, and third electrodes are in electrical contact with the right ventricle of the heart.

39. A method as defined in claim 31 wherein said first pair of locations are between first and second locations and wherein said second pair of locations are between third and fourth locations.

40. A method as defined in claim 39 further including the steps of providing first lead means including first and second electrodes, providing second lead means including third and fourth electrodes, and establishing electrical contact of said first, second, third, and fourth sensing electrodes with the heart at said first, second, third, and fourth locations respectively.

41. A method as defined in claim 40 wherein said first and second electrodes are in electrical contact with the right ventricle of the heart and wherein said third and fourth electrodes are in electrical contact with the left ventricle of the heart.

42. A method of reliably detecting a depolarization activation wave of the heart and delivering cardioverting electrical energy to the atria of the heart in synchronism with said detected depolarization activation wave, said method including the steps of:
sensing said depolarization activation wave of the heart between a first pair of spaced apart locations;
producing a first electrical output having a first predetermined characteristic corresponding to said depolarization activation wave sensed between said first pair of locations;
sensing said depolarization activation wave of the heart between a second pair of spaced apart locations;
producing a second electrical output having a second predetermined characteristic corresponding to said depolarization activation wave sensed between said second pair of locations;
comparing said first and second predetermined characteristics;
providing an indication signal indicating the occurrence of said depolarization activation wave when said first and second predetermined characteristics are different; and
applying electrical cardioverting energy to the atria of the heart responsive to said indication signal.

43. A method as defined in claim 42 wherein the spacing between said first pair of locations is different than the spacing between said second pair of locations, wherein said steps of providing said first and second electrical outputs includes the step of providing said first and second electrical outputs with durations substantially equal to the time in which said depolarization activation wave sensed between said first and second pairs of locations respectively is above a given level, and wherein said first and second predetermined characteristics are the durations of said first and second electrical outputs respectively.

44. A method as defined in claim 43 wherein said spacing between said second pair of locations is greater than the spacing between said first pair of locations and wherein said step of providing said indication signal includes providing said indication signal when said second electrical output is longer in duration than said first electrical output.

45. A method as defined in claim 42 wherein said first pair of locations are between first and second locations and wherein said second pair of locations are between said first or second location and a third location.

46. A method as defined in claim 45 further including the steps of providing first lead means including first and second electrodes, providing second lead means including a third electrode and establishing electrical contact of said first, second, and third electrodes with the heart at said first, second, and third locations respectively.

47. A method as defined in claim 46 wherein said first and second electrodes are in electrical contact with the right ventricle of the heart and wherein said third electrode is in the electrical contact with the left ventricle of the heart.

48. A method as defined in claim 45 furthest including the steps of providing a single lead means including first, second, and third electrodes and establishing electrical contact of said first, second, and third sensing electrodes with the heart at said first, second, and third locations respectively.

49. A method as defined in claim 48 wherein said first, second, and third electrodes are in electrical contact with the right ventricle of the heart.

50. A method as defined in claim 42 wherein said first pair of locations are between first and second locations and wherein said second pair of locations of the heart are between third and fourth locations.

51. A method as defined in claim 50 further including the steps of providing first lead means including first and second electrodes, providing second lead means including third and fourth electrodes, and establishing electrical contact of said first, second, third, and fourth electrodes with the heart at said first, second, third, and fourth locations respectively.

52. A method as defined in claim 51 wherein said first and second electrodes are in electrical contact with the right ventricle of the heart and wherein said third and fourth electrodes are in electrical contact with the left ventricle of the heart.

53. An apparatus for reliably detecting a depolarization activation wave of the heart, said apparatus comprising:
first sensing means for electrical contact with the heart for producing a first electrocardiographic signal of the heart;
first output means coupled to said first sensing means and responsive to said first electrocardiographic signal for isolating a predetermined feature of said first electrocardiographic signal and producing a first output characteristic of said feature of said first electrocardiographic signal;

second sensing means for electrical contact with the heart for producing a second electrocardiographic signal of the heart;

second output means coupled to said second sensing means and responsive to said second electrocardiographic signal for isolating said predetermined feature of said second electrocardiographic signal and producing a second output characteristic of said feature of said second electrocardiographic signal; and discriminating means coupled to said first and second output means and being responsive to said first and second electrical outputs for discriminating between said predetermined features of said first and second electrocardiographic signals and including indicating means for indicating the occurrence of said depolarization activation wave when said predetermined features of said first and second electrocardiographic signals are different.

54. An apparatus as defined in claim 53 wherein said first output means includes an R wave detector for detecting an R wave of said first electrocardiographic signal, wherein said second output means includes a second R wave detector for detecting an R wave of said second electrocardiograph signal, and wherein said predetermined features of said first and second electrocardiographic signals is the R wave of said electrocardiographic signals.

55. An apparatus as defined in claim 54 wherein said first and second R wave detectors each include a threshold detector for providing said first and second outputs with durations substantially equal to the time in which said R waves of said first and second electrocardiographic signals are above a given threshold, and wherein said first and second outputs are characteristic of the duration of said R waves of said first and second electrocardiograms.

56. A method of reliably detecting a depolarization activation wave of the heart, said method comprising the steps of:

sensing electrical activity of the heart at a first location of the heart and producing a first electrocardiographic signal;

isolating a predetermined feature of said first electrocardiographic signal and producing a first output characteristic of said feature of said first electrocardiographic signal;

sensing said electrical activity of the heart at a second location of the heart and producing a second electrocardiographic signal;

isolating said predetermined feature of said second electrocardiographic signal and producing a second output characteristic of said feature of said second electrocardiographic signal discriminating between said predetermined features of said first and second electrocardiographic signals; and indicating the occurrence of said depolarization activation wave when said predetermined features of said first and second electrocardiographic signals are different.

57. A method as defined in claim 56 wherein said isolating steps include detecting R waves of said first and second electrocardiographic signals and wherein said predetermined feature of said first and second electrocardiographic signals is the R wave of said electrocardiographic signals.

58. A method as defined in claim 57 wherein said isolating steps further include providing said first and second outputs with durations substantially equal to the time in which said R waves of said first and second electrocardiographic signals are above a given threshold and wherein said first and second outputs are characteristic of the duration of said R waves of said first and second electrocardiographic signals.

* * * * *

UNITED STATES PATENT AND TRADEMARK OFFICE
CERTIFICATE OF CORRECTION

PATENT NO.  : 5,348,021

DATED       : September 20, 1994

INVENTOR(S) : Adams et al.

It is certified that error appears in the above-identified patent and that said Letters Patent is hereby corrected as shown below:

| Column | Line(s) | |
|---|---|---|
| 1 | 43 | After "Unfortunately,", insert --to-- |
| 1 | 61 | After "heart", insert --is-- |
| 1 | 65 | After "such", insert --as-- |
| 1 | 68 | After "signals)", insert --in-- |
| 2 | 16 | After "tion", insert --is-- |
| 2 | 19 | After "first", insert --area-- |
| 2 | 22 | After "includes", insert --a-- |
| 2 | 32 | After "of", insert --a-- |
| 2 | 31 | After "applying", insert --a-- |
| 2 | 35 | After "waves", insert --. Noise-- |
| 2 | 37 | After "mistaken", insert --for-- |
| 2 | 43 | After "defibrillator", insert --is-- |
| 5 | 40 | After "leads", insert --34-- |
| 5 | 67 | After "coronary", insert --sinus-- (first occurrence) |
| 6 | 5 | After "lead", insert --36-- |
| 6 | 7 | After "between", insert --a-- |
| 6 | 23 | After "44", insert --is-- |
| 6 | 39 | After "microprocessor", insert --60-- |
| 7 | 62 | After "which", insert --is-- |
| 8 | 15 | After "lead", insert --36-- |
| 8 | 19 | After "generator", insert --66-- |
| 8 | 20 | After "cardioversion", insert --or-- |
| 8 | 65 | After "detector", insert --56,-- |
| 8 | 66 | After "electrocardiogram", insert --is-- |
| 9 | 4 | After "constant", insert --in-- |
| 9 | 7 | "duratic, n" should be --duration-- |
| 9 | 13 | After "that", insert --a-- |
| 9 | 28 | After "38", insert --,-- |

UNITED STATES PATENT AND TRADEMARK OFFICE
CERTIFICATE OF CORRECTION

PATENT NO.  : 5,348,021
DATED       : September 20, 1994
INVENTOR(S) : Adams et al.

It is certified that error appears in the above-identified patent and that said Letters Patent is hereby corrected as shown below:

| Column | Line(s) | |
|---|---|---|
| 10 | 54 | After "heart" delete "for" |
| 12 | 16 | After "are", insert --in-- |
| 12 | 18 | After "are", insert --in-- |
| 13 | 17 | "atria;" should be --atrial-- |
| 13 | 35,36 | "electrodes" should be --electrode-- |
| 13 | 49 | "196" should be --19-- |
| 13 | 61 | "electrodes" should be --electrode-- (second occurrence) |
| 14 | 2 | "location" should be --locations-- |
| 14 | 8 | After "are", insert --in-- |
| 15 | 8 | "of" should be --at-- |
| 16 | 19 | After "between", insert --one of-- |
| 16 | 20 | "or" should be --and-- |
| 16 | 20 | "location" should be --locations-- (first occurrence) |
| 16 | 33 | "furthest" should be --further-- |
| 18 | 17 | Insert --;-- after "signal" |

Signed and Sealed this

Fifteenth Day of November, 1994

Attest:

BRUCE LEHMAN

Attesting Officer    Commissioner of Patents and Trademarks